United States Patent [19]

Hassel et al.

[11] Patent Number: 4,600,771

[45] Date of Patent: Jul. 15, 1986

[54] PROCESS FOR THE PREPARATION OF ACYLATED SUGARS WITH A GLYCOSIDICALLY BONDED ISOTHIOCYANATE GROUP

[75] Inventors: Tillmann Hassel, Cologne; Hanns P. Müller, Odenthal, both of Fed. Rep. of Germany

[73] Assignee: Bayer Aktiengesellschaft, Leverkusen, Fed. Rep. of Germany

[21] Appl. No.: 670,691

[22] Filed: Nov. 13, 1984

[30] Foreign Application Priority Data

Nov. 12, 1983 [DE] Fed. Rep. of Germany ....... 3341018

[51] Int. Cl.$^4$ ............................................. C07H 5/06
[52] U.S. Cl. ..................... 536/22; 536/18.7; 536/55.3
[58] Field of Search ............... 536/22, 55.2, 18.7, 536/17.2, 55.3

[56] References Cited

U.S. PATENT DOCUMENTS

| | | | |
|---|---|---|---|
| 3,133,912 | 5/1964 | Kimmig et al. | 536/18.7 |
| 3,158,598 | 11/1964 | Morel | 536/55.2 |
| 4,025,622 | 5/1977 | Ogura et al. | 536/22 |
| 4,115,447 | 9/1978 | Diamond | 536/17.2 |

OTHER PUBLICATIONS

Khorlin et al., "Chem. Abst.", vol. 83, 1975, p. 92905p.
Pigman et al., "Chemistry of the Carbohydrates", 1948, Academic Press, Inc., New York, N.Y., pp. 383–384.

*Primary Examiner*—Johnnie R. Brown
*Attorney, Agent, or Firm*—Sprung, Horn, Kramer & Woods

[57] ABSTRACT

Acylated sugars with a glycosidically bonded isothiocyanate group are prepared by reacting acylated sugars with a glycosidically bonded halogen atom with thiocyanates in the presence of a phase transfer catalyst.

15 Claims, No Drawings

PROCESS FOR THE PREPARATION OF ACYLATED SUGARS WITH A GLYCOSIDICALLY BONDED ISOTHIOCYANATE GROUP

The invention relates to a process for the preparation of acylated sugars with a glycosidically bonded isothiocyanate group using phase transfer catalysts.

Acylated sugars with a glycosidically bonded isothiocyanate group are known per se. They are prepared by reacting acylated sugars with a glycosidically bonded halogen atom with certain heavy metal thiocyanates. Thus, according to Japanese Preliminary Published Application No. 77,195,123, silver thiocyanate is used as the heavy metal thiocyanate. The use of lead thiocyanate for the same purpose is described in Heterocycles 17, 87 (1982). When ammonium thiocyanate is used, the corresponding thiocyanate is formed (Heterocycles 17, 87 (1982)) and not, as earlier assumed (CA 91,14117d (1978)), the desired isothiocyanate.

The use of heavy metal thiocyanates is a disadvantage of the known processes for the preparation of acylated sugars with a glycosidically bonded isothiocyanate group. These heavy metal thiocyanates, which are already in themselves expensive, are not substances which are industrially available, but have to be prepared by expensive preparation processes. In addition, heavy metal compounds are in general toxic and require special working up processes.

A process has been found for the preparation of acylated sugars with a glycosidically bonded isothiocyanate group from acylated sugars with a glycosidically bonded halogen atom, in which the acylated sugars with a glycosidically bonded halogen atom are reacted with at least the equivalent amount of a thiocyanate of the formula $$\text{Me—NCS} \qquad (I)$$

in which Me denotes an alkali metal, an alkaline earth metal or ammonium,
in an inert solvent at elevated temperature, in the presence of a phase transfer catalyst.

In the process according to the invention, acylated sugars with a glycosidically bonded isothiocyanate group are obtained without using heavy metal thiocyanates. Surprisingly, the isothiocyanates are obtained in the process according to the invention and not, as was to be expected from Maygar Biol. Kutató Munkái 13, 525 (1941) and Synthesis 184 (1977), the thiocyanates. According to the invention, the acylated sugars with a glycosidically bonded isothiocyanate group are obtained in high yields and in a high purity.

The process according to the invention can be illustrated with the aid of the following equation:

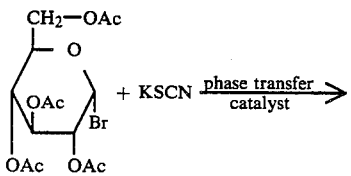

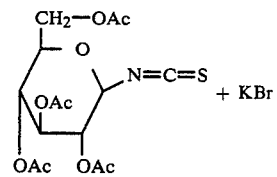

wherein Ac represents

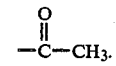

Acylated sugars with a glycosidically bonded halogen atom are known per se (F. Micheel, Chemie der Zucker und Polysaccharide (Chemistry of Sugars and Polysaccharides), 2nd edition, 1956, pages 455–456 and pages 476–477; Geest and Portig, Leipzig (1956). They can be prepared, for example, by exhaustively acylating a sugar with excess acid anhydride and then, by transesterification with anhydrous hydrogen halide, replacing the ester group on the glycosidic carbon atom by the halogen atom of the hydrogen halide employed.

The glycosidically bonded halogen atom can be fluorine, chlorine, bromine or iodine, preferably chlorine or bromine.

Examples of acylated sugars with a glycosidically bonded halogen atom are compounds of the formula

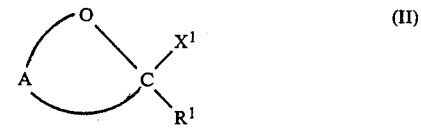

in which
$R^1$ denotes hydrogen or acyloxymethylene,
A represents one of the radicals

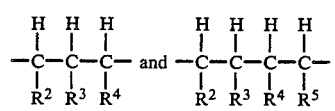

in which $R^2$ to $R^5$ are identical or different and denote hydrogen, acylamino, acylthio, nitro, azido, organosulphonyloxy, acyl ester or acyloxymethylene wherein one of the radicals $R^2$ to $R^5$ can also be another sugar residue of the formula

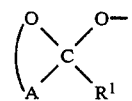

in which
$R^1$ and A have the abovementioned meaning and
$X^1$ denotes halogen.
In the

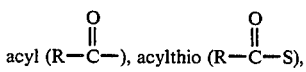

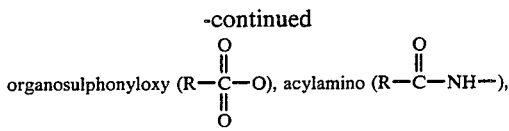

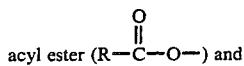

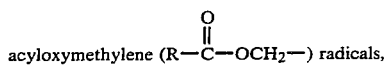

the organic radical (R) in general denotes a straight-chain or branched hydrocarbon radical with 1 to 12, preferably 1 to 8, carbon atoms. Preferred radicals are lower acyl, lower acylthio, lower organosulphonyloxy, lower acylamino, lower acyl ester and lower acyloxymethylene with 1 to about 6 carbon atoms in the organic radical.

The following radicals may be mentioned as examples: acyl radicals, such acetyl, propionyl, pivaloyl, benzoyl and 4-methylbenzoyl; acylthio radicals, such as acetylthio, butyrylthio and benzoylthio; organosulphonyloxy, such as methanesulphonyloxy, benzensulphonyloxy and 4-methyl-benzenesulphonyloxy; acylamino, such as acetylamino, 2-methylpropionylamino, benzoylamino and butyrylamino; acyl esters, such as acetoxy, propionyloxy, benzoyloxy, pivaloyloxy and butyryloxy; and acyloxymethylene, such as acetoxymethylene, benzoyloxymethylene, propionyloxymethylene, butyryloxymethylene and pivaloyloxymethylene.

It is also possible for the sugar residue to be linked to other sugar residues to form disaccharides, oligosaccharides or polysaccharides. However, mono-, di- and oligo-saccharides with 1 to 6, preferably 1 or 2, sugar residues in the molecule are preferred for the process according to the invention.

Acylated sugars with a glycosidically bonded halogen atom which are preferred for the process according to the invention are compounds of the formula

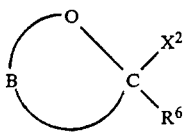

(III)

in which
R$^6$ denotes hydrogen or lower acyloxymethylene,
B represents one of the radicals

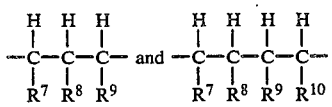

in which R$^7$ to R$^{10}$ are identical or different and denote
hydrogen, lower acylamino, lower acyl ester, lower organosulphonyloxy or lower acyloxymethylene and
wherein one of the radicals R$^7$ to R$^{10}$ can also be another sugar residue of the formula

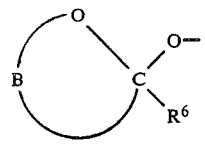

in which
R$^6$ and B have the abovementioned meaning and
X$^2$ denotes chlorine or bromine.

The following acylated sugars with a glycosidically bonded halogen atom may be mentioned specifically: 2,3,4,6-tetraacetyl-D-glucopyranosyl bromide; 2,3,4-tribenzoyl-D-ribopyranosyl bromide; 2,3,5-tribenzoyl-D-ribofuranosyl bromide; 2,2′,3,3′,4′,6,6′-heptaacetyl-D-lactosyl bromide; 2,2′,3,3′,4′,6,6′-heptaacetyl-D-cellobiosyl bromide; 2,2′,3,3′,4′,6,6′-heptaacetyl-D-maltosyl bromide, and also 2-acetamido-2-deoxy-3,4,6-triacetyl-D-glucopyranosyl chloride and 2-(4-methyl)benzenesulphonyloxy-2-deoxy-3,4,6-triacetyl-D-glucopyranosyl bromide.

Thiocyanates for the process according to the invention are alkali metal thiocyanates, alkaline earth metal or ammonium thiocyanate. Alkali metal and alkaline earth metal in the context of the process according to the invention means metals of the first and second group of the periodic table according to Mendeleev. Lithium, sodium and potassium may be mentioned as preferred.

Preferred thiocyanates for the process according to the invention are ammonium thiocyanate, sodium thiocyanate and potassium thiocyanate.

An equivalent amount or an excess of the thiocyanates is employed in the process according to the invention. In general, 1 to 10, preferably 1 to 5, equivalents of the thiocyanate, based on the acylated sugars with a glycosidically bonded halogen atom, are employed.

The process according to the invention is carried out in the presence of inert solvents, that is to say solvents which do not change under the reaction conditions. The process according to the invention can preferably be carried out in inert solvents in which the thiocyanate is virtually insoluble. According to the invention, "virtually insoluble" is understood as meaning a solubility of below 0.1%.

Examples of solvents for the process according to the invention are straight-chain, branched or cyclic aliphatic ethers, such as dibutyl ether and dioxane, aliphatic nitriles, such as acetonitrile, esters and ketones, such as butyl acetate and propanone, aromatic hydrocarbons, such as benzene, and araliphatic hydrocarbons, such as toluene, ethylbenzene and the isomeric xylenes.

Preferred solvents for the process according to the invention are aromatic and aliphatic hydrocarbons. Benzene, toluene, ethylbenzene and xylene may be mentioned in particular.

The solvents can of course also be used as mixtures.

In general, 1 to 20, preferably 2 to 12, parts by weight of the inert solvent, based on the sugar derivative employed, are used.

The process according to the invention is carried out in the presence of a phase transfer catalyst, which preferably has a complexing constant of 170 L/mol to 10$^8$ L/mol. Phase transfer catalysts with a complexing constant of 450 L/mol to 10$^6$ L/mol are particularly preferred.

The complexing constant is to be understood here as meaning the equilibrium constant for the formation of ion pairs with an inserted phase transfer catalyst in solutions of sodium fluorenyl in tetrahydrofuran or tetrahydropyran (Kontakte 1977, Issue 2, page 20 et seq.).

Polyethers are preferred phase transfer catalysts for the process according to the invention.

The polyethers for the process according to the invention are built up from ethylene oxide units and can be linear or cyclic.

Linear polyethers as phase transfer catalysts according to the invention are in general used with a molecular weight of 150 to 2000, preferably of 190 to 1000.

The following linear polyethers may be mentioned as examples: tetraethylene glycol, hexaethylene glycol, octaethylene glycol and decaethylene glycol.

The linear polyethers can also be used in the form of industrial mixtures with average molecular weights of 200 to 2000, preferably of 400 to 1000.

The following polyethers may be mentioned as examples: polyethylene glycol of $\overline{M}=400$, polyethylene glycol of $\overline{M}=650$ and polyethylene glycol of $\overline{M}=1000$.

The H atoms of the terminal OH groups of the polyethers can optionally be replaced by alkyl radicals. The alkyl radicals can be linear or branched with a carbon number of 1 to 6. Linear alkyl radicals with a carbon number of 1 or 2 are preferred. The following polyethers with terminal alkyl groups may be mentioned as examples: hexaethylene glycol dimethyl ether, the dimethyl ether of polyethylene glycol of $\overline{M}=400$, the diethyl ether of polyethylene glycol of $\overline{M}=650$ and octaethylene glycol dipropyl ether.

Polyethers as phase transfer catalysts according to the invention can also be macrocyclic polyethers with a ring size of 12 to 24 atoms, preferably of 15 to 18 atoms.

In these macrocyclic polyethers, it is also possible for one or more, preferably one or two, ethylene groups to be replaced by one or more, preferably one or two, aromatic and/or aliphatic ring systems of carbon number 5 to 10, preferably 6, such that the oxygen atom bonded to the particular ethylene groups replaced are separated by two carbon atoms of the corresponding aromatic or aliphatic ring system. Such polyethers are described, for example, in U.S. Pat. No. 3,686,225.

The following macrocyclic polyethers may be mentioned as examples: 1,4,7,10-tetraoxacyclododecane, 1,4,7,10,13-pentaoxacyclopentadecane, 1,4,7,10,13,16-hexaoxacyclooctadecane, 2,5,8,15,18,21-hexyoxatricyclo[20.4.0.0$^{9.14}$]hexacosane, 2,5,8,11,14,17-hexaoxabicyclo[16.4.0]docosane, 2,3,11,12-dibenzo-1,4,7,10,13,16-hexaoxacyclooctadeca-2,11-diene and 2,3-benzo-1,4,7,10,13-pentaoxacyclopentadeca-2-ene.

To facilitate recovery of the polyethers according to the invention, it may be advantageous to modify them by known chemical reactions (for example formylation in the case of polyethers with aromatic ring systems), to bond the modified polyethers to a polymeric carrier, in a manner which is likewise known per se, and to use the polyethers modified in this manner in the process according to the invention.

Phase transfer catalysts such as the dimethyl ether of polyethylene glycol of $\overline{M}=400$, octaethylene glycol dipropyl ether, the diethyl ether of polyethylene glycol of $\overline{M}=650$, 1,4,7,10,13-pentaoxacyclopentadecane, 1,4,7,10,13,16-hexaoxacyclooctadecane, 2,5,8,15,18,21-hexaoxatricyclo[20.10.13.16]hexaoxacyclooctadecane, 2,5,8,15,18,21-hexaoxatricyclo[20.4.0.0$^{9.14}$]hexacosane, 2,3,11,12-dibenzo-1,4,7,10,13,16-hexaoxacyclooctadeca-2,11-diene and 2,3-benzo-1,4,7,10,13-pentaoxacyclopentadeca-2-ene are particularly preferred for the process according to the invention.

In general, 0.1 to 10 mol %, preferably 1 to 5 mol %, of the phase transfer catalyst, based on the acylhalogeno-sugar employed, is used for the process according to the invention.

The process according to the invention is carried out at elevated temperature. In general, the process according to the invention is carried out in the temperature range from 20° to 150° C., preferably in the temperature range from 80° to 110° C.

The process according to the invention is in general carried out under normal pressure. However, it is of course also possible to carry out the process according to the invention under a reduced or increased pressure (for example in the pressure range from 0.5 to 10 bar). The end of the reaction can easily be monitored by physical methods, for example spectroscopically. In general, the reaction has ended after a reaction time of 3 to 30 hours, preferably of 6 to 24 hours.

The process according to the invention can be carried out, for example, as follows:

The acylated sugar with a glycosidically bonded halogen atom is taken in the solvent together with the thiocyanate and the phase transfer catalyst. The reaction mixture is heated up to the desired reaction temperature, with vigorous stirring. The reaction mixture is stirred until the reaction has ended.

When the reaction has ended, the insoluble constituents are separated off. From the organic solution the desired acylated sugar with a glycosidically bonded isothiocyanate group is isolated in a manner which is known per se, by distillation and recrystallization.

Acylated sugars with a glycosidically bonded isothiocyanate group of the formula

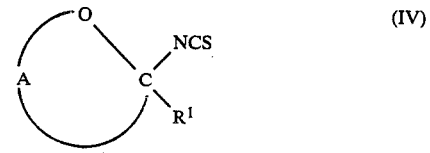

(IV)

in which

R$^1$ denotes hydrogen or acyloxymethylene,

A represents one of the radicals

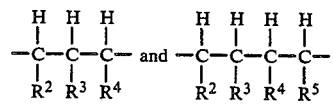

in which R$^2$ to R$^5$ are identical or different and denote hydrogen, acylamino, acylthio, nitro, azido, organosulphonyloxy, acyl ester or acyloxymethylene, and wherein one of the radicals R$^2$ to R$^5$ can also be another sugar residue of the formula

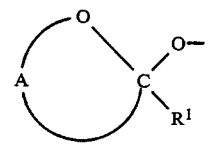

in which R$^1$ and A have the abovementioned meaning, can be prepared by the process according to the invention.

Acylated sugars with a glycosidically bonded isothiocyanate group are important organochemical intermediates. They either already have themselves an active compound character, or are used as components for building up new active compounds or for modifying known substances (DE-OS No. 25 09 260, European Pat. No. 24,202 and DDR Patent Specification No. 34,860). Thus 1-(2,3,4,6-tetraacetyl-$\beta$-D-glucosyl)-4-S-methylisothioburet can be prepared in a manner known per se (Ogura et al: Chem. Pharm. Bull. 29, 1938 (1981)) from the 2,3,4,6-tetraacetyl-$\beta$-D-glucosyl-1-isothiocyanate obtainable by the process according to the invention by reaction with S-methyl-isothiourea iodide. By splitting off the acetyl groups by known methods the nematicidally active 1-$\beta$-D-glucosyl-4-S-methylisothioburet (Example 9) is obtained from this isothioburet.

EXAMPLE 1

50 g (121.7 mmol) of acetobromoglucose, 11.8 g (121.7 mmol) of potassium thiocyanate and 0.3 g (1.14 mmol) of 1,4,7,10,13,16-hexaoxacyclooctadecane in 150 ml of toluene are taken in a flask with a magnetic stirrer and a reflux condenser with a drying tube. The mixture is stirred under reflux (110° C.) for 7 hours and the insoluble material is filtered off hot. On cooling, 32.32 g (83.1 mmol) of 2,3,4,6-tetraacetyl-$\beta$-D-glycosyl 1-isothiocyanate crystallize out of the filtrate.

A further 4.3 g (11.05 mmol) of product can be obtained from the mother liquor after concentration and recrystallization with diisopropyl ether.

Total yield: 36.62 g (94.14 mmol)=77.4%, melting point: 113° C.

EXAMPLE 2

10 g (24.5 mmol) of acetobromoglucose, 2.401 g (24.5 mmol) of potassium thiocyanate and 100 mg (0.25 mmol) of the dimethyl ether of polyethylene glycol of $\overline{M}$=400 in 25 ml of toluene are taken in a flask with a magnetic stirrer and a reflux condenser with a drying tube. The mixture is boiled under reflux for 20 hours and filtered hot with suction. On cooling, 6.2 g (15.94 mmol) of the isothiocyanate of Example 1 crystallize out of the filterate.

Yield: 65%, melting point: 113° C.

EXAMPLE 3 (comparison example)

The batch from Example 2 is repeated *without* addition of a phase transfer catalyst. After filtration with suction, no precipitate is obtained from the filtrate. The product isolated from the filtrate by distilling off the toluene has an indefinite melting point of between 86° and 94° C.

EXAMPLE 4

16 g (22.89 mmol) of acetobromocellobiose, 2.22 g (22.89 mmol) of potassium thiocyanate and 56.5 mg of 1,4,7,10,13,16-hexaoxacyclooctadecane are taken in 180 ml of toluene. The mixture is heated at 110° C. for 7 hours and fitlered hot with suction. On cooling, 10.9 g of heptaacetylcellobiosyl 1-isothiocyanate of melting point 209° C. crystallize out of the filtrate.

Yield: 10.9 g=16.1 mmol=70.33%.

EXAMPLE 5

20 g (48.68 mmol) of acetobromoglucose, 4.72 g (48.7 mmol) of potassium thiocyanate and 60 mg of 1,4,7,10,13,16-hexaoxacyclooctadecane are taken in 70 ml of acetonitrile. The mixture is boiled under reflux for 8 hours and filtered hot with suction and the acetonitrile is distilled off from the filtrate in vacuo. The residue is recrystallized from 10 ml of toluene and washed twice with 5 ml of ice-cold toluene. 11 g of product are obtained.

Yield: 11 g=28.28 mmol=58%.

EXAMPLE 6

10.25 g (25 mmol) of acetobromoglucose, 2.1 g (25 mmol) of sodium thiocyanate and 55 mg (0.25 mmol) of 1,4,7,10,13,16-hexaoxacyclooctadecane are taken in 30 ml of toluene. The mixture is heated at 110° C. for 7 hours and fitlered hot with suction. On cooling, 6.76 g of the product from Example 1 crystallize out of the filtrate.

Yield: 6.76 g=17.4 mmol=69.6%.

EXAMPLE 7

The batch from Example 6 is repeated, but the sodium thiocyanate is replaced by 1.9 g (25 mmol of ammonium thiocyanate.

4.56 g of the product from Example 1 are obtained.

Yield: 4.56 g=11.8 mmol=47.2%

EXAMPLE 8

4.51 g (8.37 mmol) of 2-(4-methyl)-benzosulphonyloxy-2-deoxy-3,4,6-triacetyl-D-glucopyranosyl bromide, 0.81 g (8.37 mmol) of potassium thiocyanate and 185 mg (0.837 mmol) of 1,4,7,10,13,16-hexaoxacyclooctadecane are taken in 40 ml of toluene. The mixture is heated at 110° C. for 7 hours and filtered with suction. The filtrate is cooled to −20° C. 1.8 g (3.6 mmol) of 2-(4-methyl)benzosulphonyl-2-deoxy-3,4,6-triacetyl-$\beta$-D-glucopyranosyl 1-isothiocyanate crystallize.

Yield: 1.8 g=3.6 mmol=43%.

Melting point: 150° C.

EXAMPLE 9 (Use example)

1-$\beta$-D-Glucosyl-4-S-methylisothioburet 40 ml of triethylamine are added dropwise to a solution, which has a temperature of 40° C., of 20.76 g (95.2 mmol) of S-methylisothiourea iodide and 37.03 g (95.2 mmol) of 2,3,4,6-tetraacetyl-$\beta$-D-glucosyl-1-isothiocyanate in 100 ml of acetonitrile. An exothermic reaction takes place. The mixture is evaporated to dryness, the residue is dissolved in chloroform and extracted twice with water. The organic phase is separated off, dried (MgSo$_4$), filtered and evaporated. The residue is recrystallized from ethanol. 39.6 g (81.5 mmol)=85.6% of protected isothioburet of a melting point of 169° C. is obtained.

30 g (62 mmol) of this protected isothioburet are dissolved in 200 ml of anhydrous methanol, 168 mg (31 mmol) of sodium methanolate are added and the mixture is stirred at room temperature with the exclusion of moisture. A colorless precipitate of 1-$\beta$-D-glucosyl-4-S-methylisothioburet is produced. This is filtered off and dried. 12.3 g (39.2 mmol) of a product having a melting point of 184° C. is obtained.

Yield: 12.3 g=39.2 mmol=63.2%

Melting point: 184° C.

The test for nematicidal action (test organism: *Heterodera rostochiensis*) gave the following results:

100% action in the case of a product concentration of 40 ppm,

95% action in the case of a product concentration of 20 ppm.

What is claimed is:

1. A process for the preparation of an acylated sugar with a glycosidically bonded isothocyanate group which comprises contacting an acylated sugar having a glycosidically bonded halogen atom with at least 1 equivalent of a thiocyanate of the forula

wherein
Me denotes an alkali metal, an alkaline earth metal or ammonium, in an inert solvent in which said thiocyanate is virtually insoluble at an elevated temperature in the presence of a phase transfer catalyst having a complexing constant of 170 L/mol to $10^8$ L/mol.

2. A process according to claim 1 wherein said thiocyanate is sodium thiocyanate, potassium thiocyanate or ammonium thiocyanate.

3. A process according to claim 1 wherein 1 to 2 equivalents of thiocyanate are employed per equivalent of said acylated sugar with a glycosidically bonded halogen atom.

4. A process according to claim 1 wherein said phase transfer catalyst is a polyether of ethylene oxide units.

5. A process according to claim 1 wherein said phase transfer catalyst is a polyether, the hydrogen atoms of the terminal hydroxyl groups of which had been replaced by alkyl radicals.

6. A process according to claim 1 wherein said phase transfer catalyst is a linear polyether having an average molecular weight of 200 to 2,000.

7. A process according to claim 1 wherein said phase transfer catalyst is a macrocyclic polyether with a ring size of 12 to 24 carbon atoms.

8. A process according to claim 1 wherein said acylated sugar with a glycosidically bonded halogen atom is one having the formula

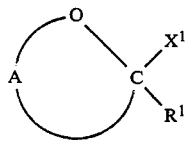 (II)

wherein
$R^1$ denotes hydrogen or acyloxymethylene,
A represents one of the radicals

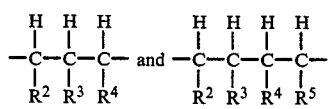

wherein
$R^2$ to $R^5$ are identical or different and denote hydrogen, acylamino, acylthio, nitro, azido, organosulphonyloxy, acyl ester or acyloxymethylene
wherein
one of the radicals $R^2$ to $R^5$ can also be another sugar residue of the formula

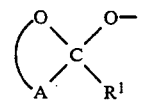

wherein
$R^1$ and A have the abovementioned meaning and
$X^1$ denotes halogen.

9. A process according to claim 8 wherein the acyl group is an organo acyl group.

10. A process according to claim 1, wherein said acylated sugar with a glycosidically bonded halogen atom is one of the formula

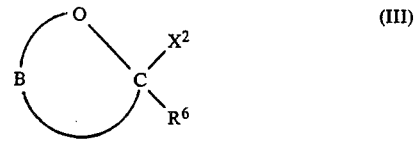 (III)

wherein
$R^6$ denotes hydrogen or lower acyloxymethylene,
B represents one of the radicals

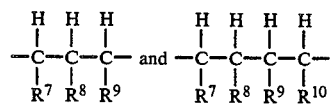

wherein
$R^7$ to $R^{10}$ are identical or different and denote hydrogen, lower acylamino, lower acyl ester, lower organosulphonyloxy or lower acyloxymethylene and
wherein
one of the radicals $R^7$ to $R^{10}$ can also be another sugar residue of the formula

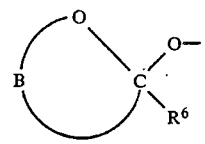

wherein
$R^6$ and B have the abovementioned meaning and
$X^2$ denotes chlorine or bromine.

11. A process according to claim 1 wherein said acylated sugar is acetobromoglucose.

12. A process according to claim 1 wherein said acylated sugar is acetobromocellobiose.

13. A process according to claim 1 wherein said acylated sugar is 2-(4-methyl)-benzosulphonyloxy-2-deoxy-3,4,6-triacetyl-D-glucopyranosyl bromide.

14. A process according to claim 1 wherein said phase transfer catalyst is 1,4,7,10,13,16-hexaoxacyclooctadecane.

15. A process according to claim 1 wherein said phase transfer catalyst is the dimethylether of polyethyleneglycol of $\overline{M}=400$.

* * * * *